(12) United States Patent
Haarala et al.

(10) Patent No.: US 8,137,316 B2
(45) Date of Patent: Mar. 20, 2012

(54) SHEATHLESS INSERTION STYLET SYSTEM FOR CATHETER PLACEMENT

(75) Inventors: Brett Haarala, Framingham, MA (US); Richard Braga, Taunton, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 46 days.

(21) Appl. No.: 12/041,384

(22) Filed: Mar. 3, 2008

(65) Prior Publication Data

US 2009/0112167 A1  Apr. 30, 2009

Related U.S. Application Data

(60) Provisional application No. 60/904,481, filed on Mar. 2, 2007.

(51) Int. Cl.
*A61M 5/178* (2006.01)

(52) U.S. Cl. .............. 604/164.01; 604/170.02; 604/533; 604/537

(58) Field of Classification Search ............. 604/164.01, 604/170.02, 528, 533, 164.07, 164.09, 164.12, 604/170.01, 537; 606/1
See application file for complete search history.

(56) References Cited

U.S. PATENT DOCUMENTS

| | | | |
|---|---|---|---|
| 3,552,394 A * | 1/1971 | Horn ............................. 604/173 |
| 3,890,970 A * | 6/1975 | Gullen ..................... 604/170.02 |
| 4,270,535 A * | 6/1981 | Bogue et al. ...................... 604/44 |
| 5,405,339 A | 4/1995 | Kohnen et al. |
| 5,509,897 A | 4/1996 | Twardowski et al. |
| 5,603,703 A * | 2/1997 | Elsberry et al. ............... 604/268 |
| 5,624,413 A | 4/1997 | Markel et al. |
| 5,873,842 A | 2/1999 | Brennen et al. |
| 5,944,732 A | 8/1999 | Raulerson et al. |
| 6,638,242 B2 | 10/2003 | Wilson et al. |
| 6,702,781 B1 * | 3/2004 | Reifart et al. ............... 604/96.01 |
| 6,719,749 B1 * | 4/2004 | Schweikert et al. .......... 604/544 |
| 6,858,019 B2 | 2/2005 | McGuckin, Jr. et al. |
| 6,872,198 B1 | 3/2005 | Wilson et al. |
| 6,921,396 B1 | 7/2005 | Wilson et al. |
| 6,939,328 B2 | 9/2005 | Raulerson |
| 7,128,734 B1 | 10/2006 | Wilson et al. |
| 2004/0034324 A1 * | 2/2004 | Seese et al. ................... 604/246 |
| 2004/0065333 A1 | 4/2004 | Wilson et al. |
| 2004/0158229 A1 | 8/2004 | Quinn |
| 2004/0176739 A1 | 9/2004 | Stephens et al. |
| 2005/0027282 A1 | 2/2005 | Schweikert et al. |
| 2005/0038413 A1 | 2/2005 | Sansoucy |
| 2005/0107739 A1 | 5/2005 | Palma |
| 2006/0015130 A1 | 1/2006 | Voorhees, Jr. et al. |
| 2006/0058737 A1 | 3/2006 | Herweck et al. |
| 2006/0095062 A1 | 5/2006 | Stephens |
| 2007/0016167 A1 | 1/2007 | Smith et al. |
| 2007/0049960 A1 | 3/2007 | Stephens et al. |
| 2007/0078396 A1 | 4/2007 | Feeley et al. |
| 2008/0009784 A1 * | 1/2008 | Leedle et al. ................... 604/43 |

* cited by examiner

*Primary Examiner* — Theodore Stigell
(74) *Attorney, Agent, or Firm* — Thomas M. Johnston, Esq.

(57) ABSTRACT

A stylet instrument is positionable within a catheter to facilitate placement of the catheter during a surgical procedure. The stylet instrument has application in a hemodialysis procedure where the catheter is positioned via a subcutaneous tunneling technique. The stylet instrument includes a hub, first and second stylet members extending from the hub and operatively connected to permit positioning within corresponding lumens of a catheter, and securing means associated with the hub to releasably secure the catheter to the hub. The securing means includes at least one locking detent.

19 Claims, 10 Drawing Sheets

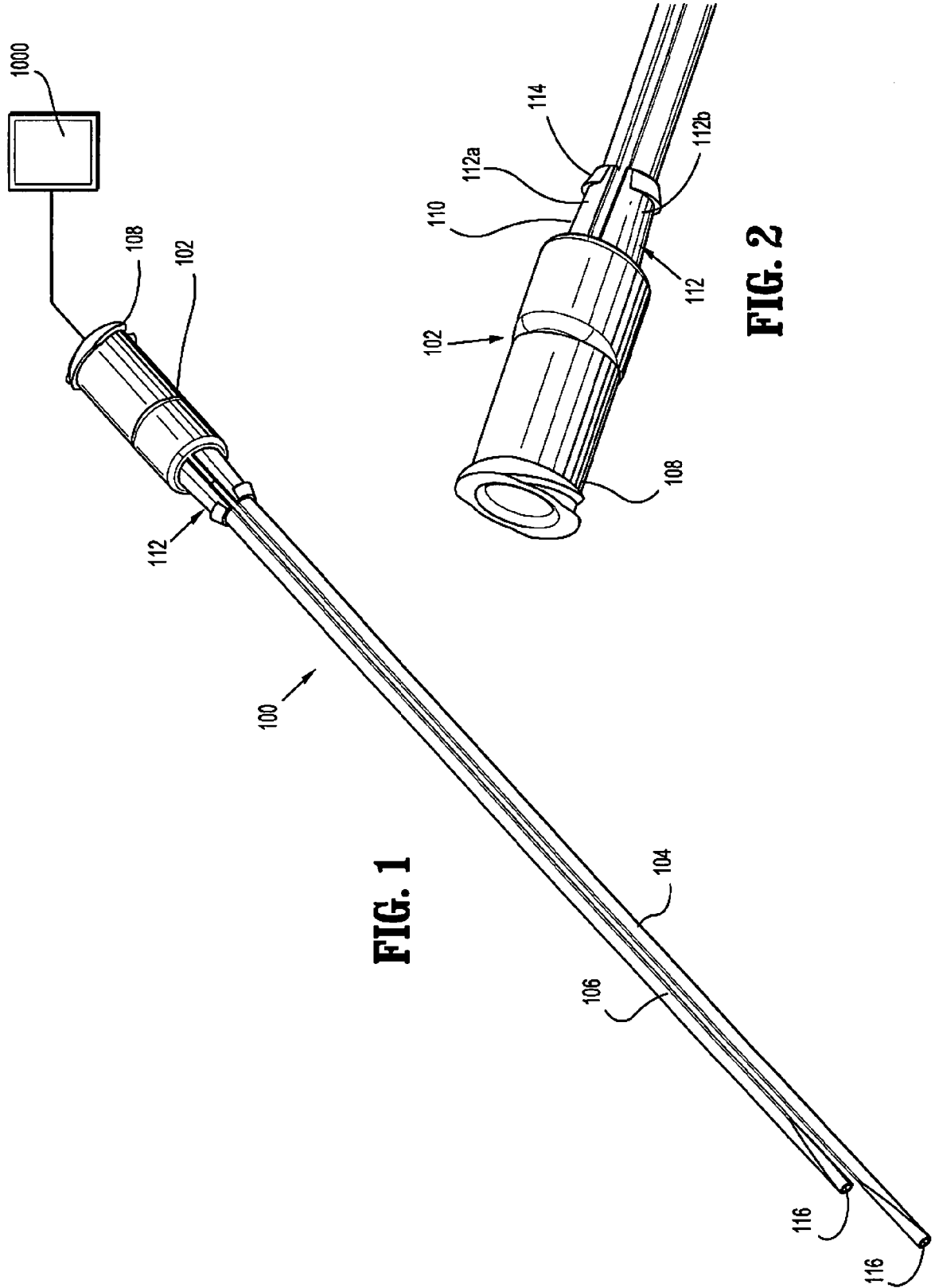

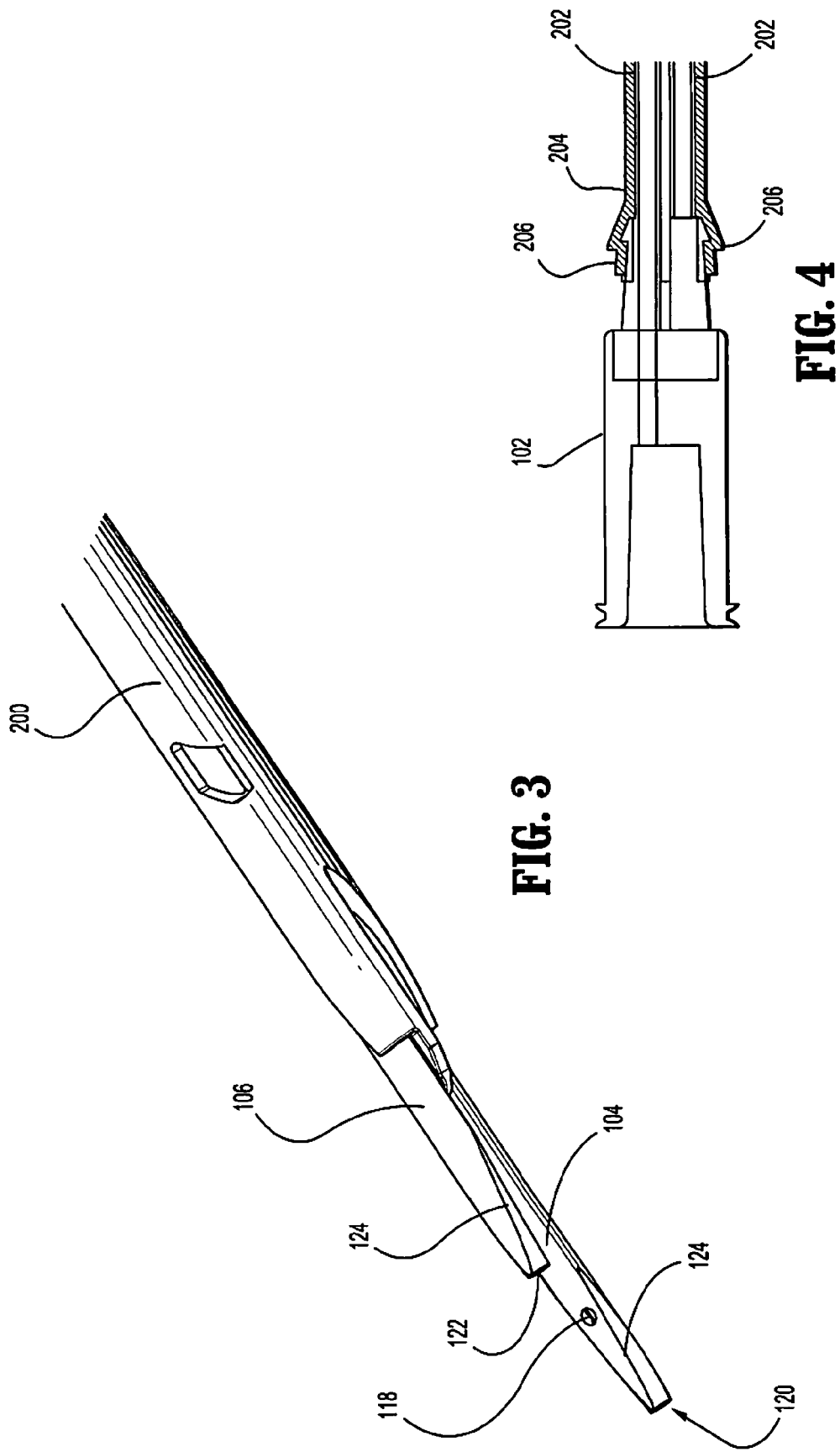

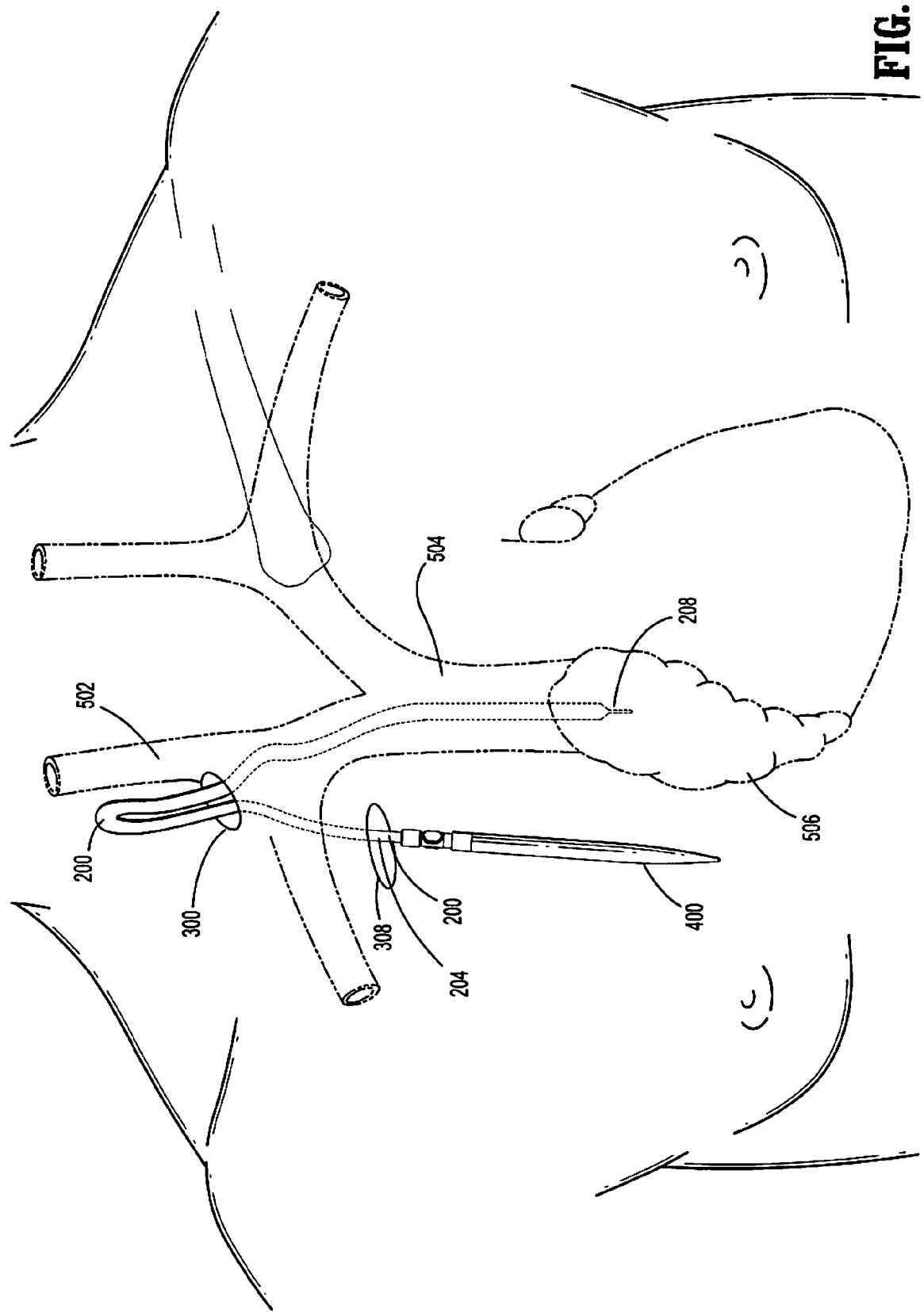

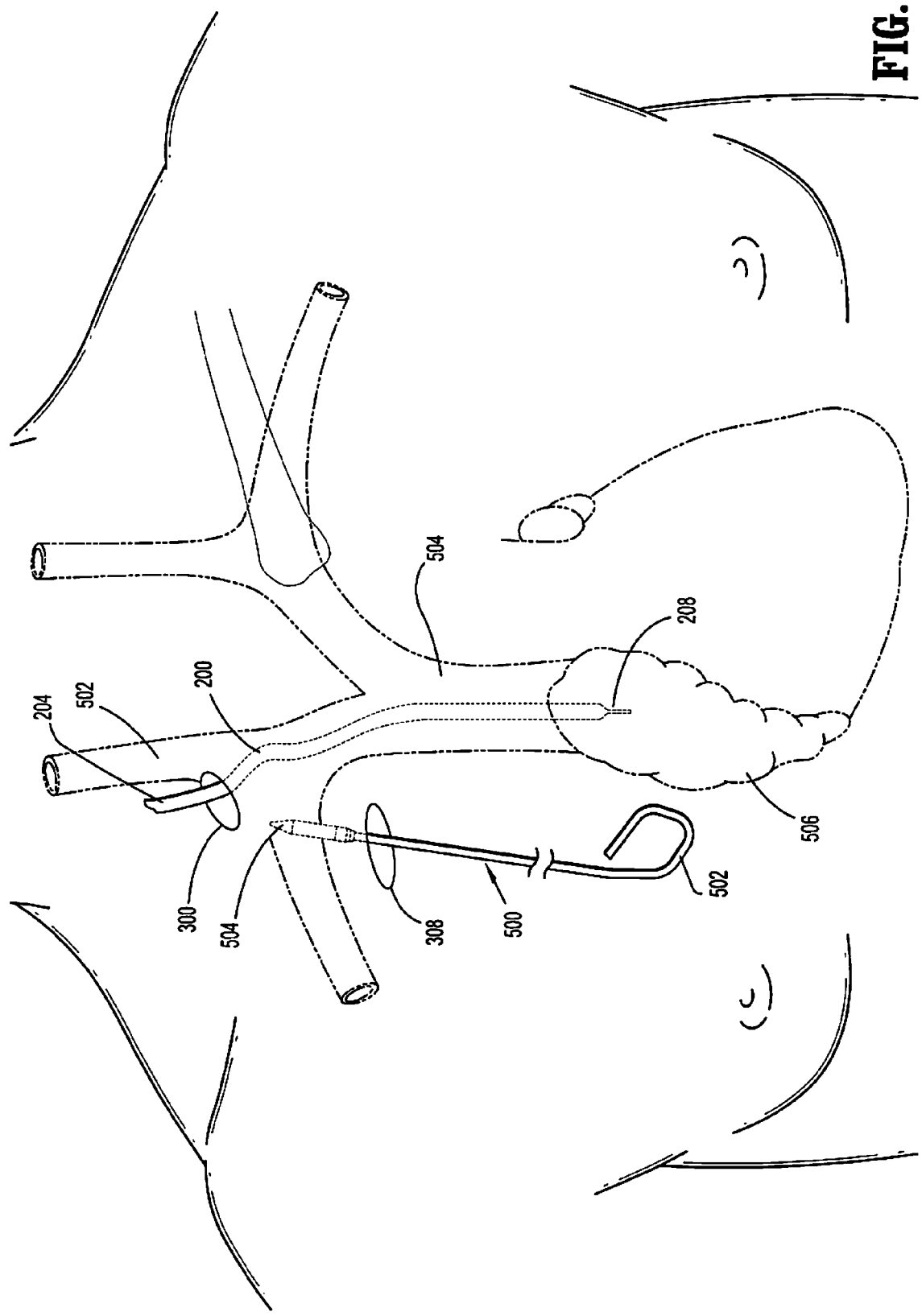

SHEATHLESS INSERTION STYLET SYSTEM FOR CATHETER PLACEMENT

CROSS REFERENCE TO RELATED APPLICATION(S)

This application claims priority to, and the benefit of, U.S. Provisional Patent Application Ser. No. 60/904,481 filed on Mar. 2, 2007.

BACKGROUND

1. Technical Field

The present disclosure relates generally to a medical catheter apparatus, and, more particularly, to a sheathless insertion stylet system for catheter placement.

2. Description of the Related Art

Catheters are flexible medical instruments intended for the withdrawal and introduction of fluids relative to body cavities, ducts, and vessels. Catheter instrumentation may have particular application in a hemodialysis procedure where blood is withdrawn from a blood vessel for treatment, and, subsequently returned to the blood vessel for circulation. Known hemodialysis catheters include multiple lumens, such as dual lumen or triple-lumen catheters, permitting bi-directional fluid flow within the catheter whereby one lumen is dedicated for withdrawal of blood and the other lumen is dedicated for returning the treated blood to the vessel. During an exemplary catheter insertion procedure, a multiple lumen catheter is inserted into a body and blood is withdrawn through an arterial lumen of the catheter. The removed blood is directed to a hemodialysis unit, which dialyzes, or purifies, the blood to remove waste and toxins. The dialyzed blood is returned to the patient through a venous lumen of the catheter.

Various techniques are employed for the insertion of hemodialysis catheters including, e.g., with the use of guidewires, introduction stylets, or the like. Some of these known techniques include subcutaneous tunneling methodologies, including ante grade and reverse tunneling techniques, where a subcutaneous tunnel is formed between two spaced openings in the skin with the use of a trocar or the like. One catheter end may be attached to the trocar and pulled though the tunnel to expose the catheter end from one of the openings. One end of the catheter may be introduced into, e.g., the jugular vein and routed to the heart. The remaining end is attached to a hemodialysis machine.

These current catheter placement techniques may result in tearing or snagging of tissue as well as patient discomfort during placement. To address such trauma, catheters are often manufactured from softer and more flexible materials. These softer and more flexible materials may require the use of a stiffener to aid in the placement of the catheter in the vessel.

Therefore, it would be desirable to have a catheter apparatus that facilitates placement within a body vessel with reduced vessel trauma and patient discomfort. It would highly desirable if the catheter apparatus and its constituent parts are easily and efficiently manufactured and assembled.

SUMMARY

Accordingly, the present disclosure is directed to a stylet instrument which is positionable within a catheter to facilitate placement of the catheter during a surgical procedure. The stylet instrument has application in a hemodialysis procedure where the catheter is positioned via a subcutaneous tunneling technique. The stylet instrument includes a hub, first and second stylet members extending from the hub and operatively connected to permit positioning within corresponding lumens of a catheter, and securing means associated with the hub to releasably secure the catheter to the hub.

In one embodiment, the stylet instrument includes a hub having a first end portion adapted for releasable connection to an external device and a second end portion defining an internal chamber and adapted for releasable connection to a catheter tube. First and second stylet members extend from the hub. Each of the first and second stylet members are dimensioned for reception within corresponding lumens of the catheter tube. The first stylet member may define a first lumen extending along at least a portion of a first length thereof and the second stylet member may define a second lumen extending along at least a portion of a second length thereof. The first end of the stylet instrument may be connected to a fluid source or to a trocar/tunneling instrument during use in implanting the catheter. The first end portion of the hub may include a luer connector.

The second end portion of the hub includes a catheter connector adapted to engage the catheter tube. The catheter connector includes a first segment and a second segment dimensioned for reception within respective lumens of the catheter tube. At least one locking detent may be incorporated with the first and second segments to engage an internal surface of the catheter to facilitate securement therewith. At least one of the first and second segments of the catheter connector has a tapered configuration for facilitating insertion into the lumens of the catheter tube.

A trocar may be integrally formed with the hub.

Methods of use of the stylet instrument in connection with tunneling procedures for hemodialysis are also disclosed.

BRIEF DESCRIPTION OF THE DRAWINGS

Embodiments of the disclosure will be better understood with reference to the accompanying drawings wherein:

FIG. 1 is a perspective view of an insertion stylet in accordance with the principles of the present disclosure illustrating the hub and the first and second stylet members extending from the hub;

FIG. 2 is an enlarged perspective view of the hub of the insertion stylet;

FIG. 3 is an enlarged perspective view of the leading end of a catheter with the first and second stylet members positioned therein;

FIG. 4 is a cross-sectional view of the hub and the proximal end of the catheter tube;

FIG. 5A is a view illustrating another step of the reverse tunneling procedure;

FIGS. 5B-5C are views illustrating an alternate tunneling procedure;

DETAILED DESCRIPTION OF THE EMBODIMENTS

Figure 5:
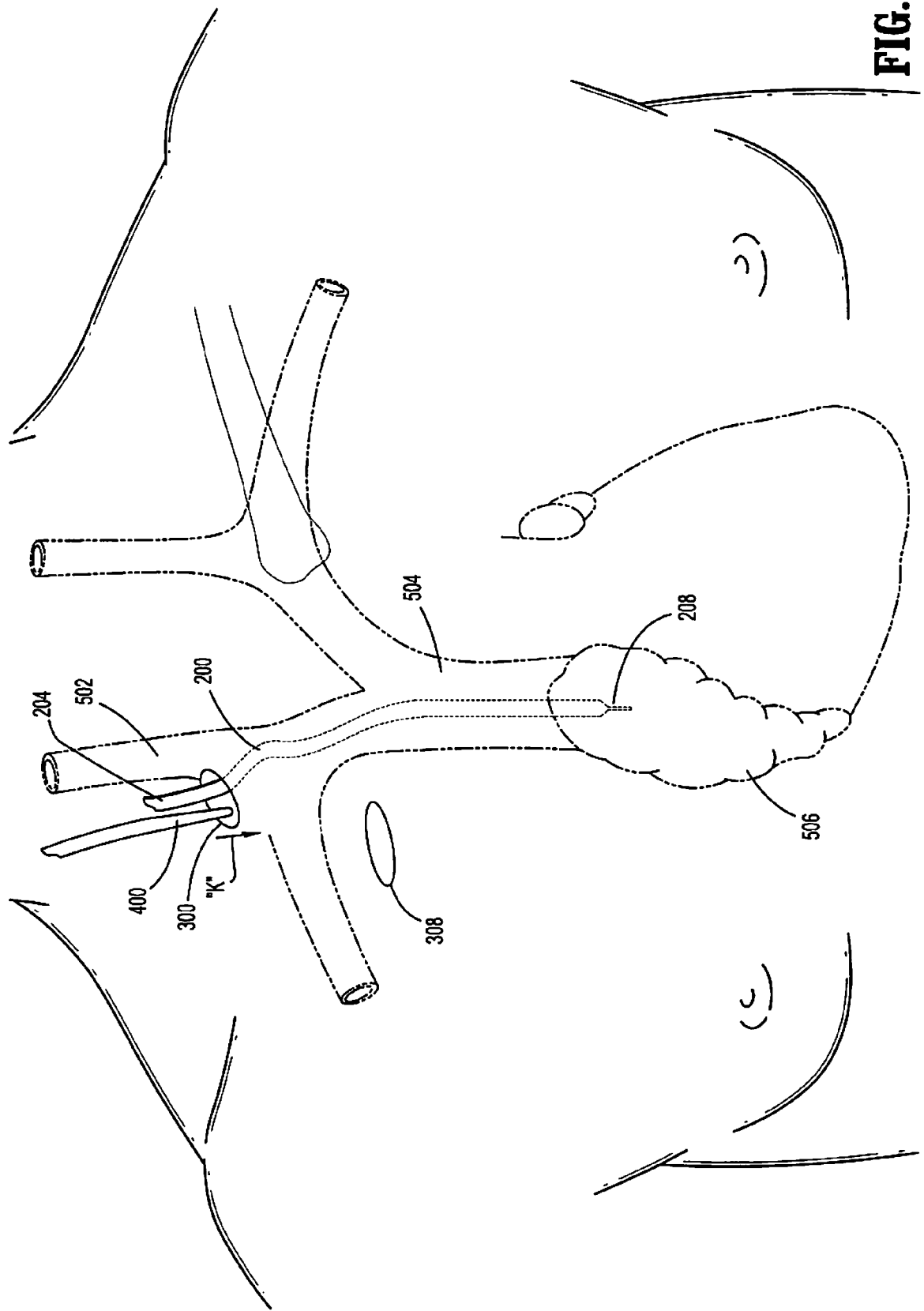
FIG. 5 is a view illustrating a reverse tunneling procedure where the stylet instrument is utilized.

The exemplary embodiments of the catheter and methods of use disclosed are discussed in terms of medical catheters for the administration of fluids (withdrawal or introduction) relative to the body of a subject and, more particularly, in terms of a hemodialysis catheter. However, it is envisioned that the present disclosure may be employed in a wide range of catheter applications including surgical, diagnostic, and related treatments of diseases and body ailments of a subject. It is further envisioned that the principles relating to the catheter disclosed include employment with various catheter related procedures, such as, for example, hemodialysis, cardiac, abdominal, urinary, intestinal, and in chronic and acute applications. Moreover, the catheter can be used for administration of fluids such as, for example, medication, saline, bodily fluids, blood, and urine.

In the discussion that follows, the term "proximal" or "trailing" will refer to the portion of a structure that is closer to a clinician, while the term "distal" or "leading" will refer to the portion that is farther from the clinician. As used herein, the term "subject" refers to a human patient or other animal. The term "clinician" refers to a doctor, nurse or other care provider and may include support personnel.

The following discussion includes a description of the insertion stylet, followed by a description of an exemplary method of operating the stylet instrument in positioning a catheter for a hemodialysis procedure. The method of operation will be discussed in terms of a subcutaneous tunneling procedure (e.g., ante grade tunneling or reverse tunneling) utilized for positioning the catheter during a dialysis procedure. However, those skilled in the art will appreciate the stylet instrument has many other applications in addition to dialysis applications.

Referring now to FIGS. 1-2, the insertion stylet for facilitating insertion of a catheter within a body vessel is illustrated. Insertion stylet 100 has particular application in use with a hemodialysis procedure to facilitate placement of the hemodialysis procedure in connection with a subcutaneous procedure. Insertion stylet 100 includes stylet hub 102 and first and second elongated stylet members 104,106 operatively connected to the stylet hub 102 and extending therefrom. Stylet hub 102 may be any suitable housing member dimensioned for manual engagement. In one embodiment, stylet hub 102 includes luer connector 108 adapted for connection to a fluid source, shown schematically as reference numeral 1000, such as a source of saline for irrigation purposes or to a source of vacuum. Luer connector 108 incorporates means, as is conventional, to facilitate securement to the fluid source. Such means includes a partial thread, bayonet coupling or the like. Stylet hub 102 further includes catheter connector end 110 for releasably securement of a catheter. Catheter connector end 110 may incorporate tapered segment 112 having a circumferential or partial circumferential locking detent 114. Locking detent 114 is adapted to engage the internal lumen to secure the catheter connector end 110 to the catheter. Catheter connector end 110 may be bifurcated, i.e., incorporating first and second segment members 112a, 112b, which are appropriately dimensioned to be received within each of the lumens of the dual lumen. First and second segment members 112a, 112b may be generally D-shaped in cross-section for reception with corresponding D-shaped lumens of the dual lumen catheter. First and second segment members 112a, 112b may be generally tapered extending radially inwardly toward locking detent 114, and may have the locking detent as discussed hereinabove. Other arrangements for the cross-section of first and second segment members 112a, 112b are envisioned including oval, circular, or polygonal.

First and second stylet members 104, 106 are secured to stylet hub 102 through any conventional means. In one embodiment, first stylet member 104 has a greater length to extend beyond second stylet member 106 as shown. First and second stylet members 104,106 may include internal lumens 116 extending completely along their lengths for reception of a guidewire and/or permit flushing or aspirating capabilities. As a further option, first stylet member 104 may include an opening 118 in its outer wall spaced from its outlet end 120 and in communication with the internal lumen 116 of the first stylet member 104. In use with a guidewire, the free end of the guidewire is introduced within the outlet end 120 of the first stylet member 104 and passed through opening 118. Thereafter the guidewire is introduced through the outlet end 122 leading to lumen 116 of second stylet member 106 and passed along the second stylet member 106 for extension out the back end of the second stylet member 106. First and second stylet members 104, 106 may have a chamfered surface 124 adjacent their outlet ends 120,122 to facilitate initial passage of the first and second stylet members 104, 106 through catheter. First and second stylet members 104, 106 may have some bending capabilities to assist in navigating through the vessel and possibly the subcutaneous tissue.

FIGS. 3-4 illustrate insertion of first and second stylet members 104, 106 of stylet instrument 100 within a catheter 200. One suitable catheter 200 may be the catheter extrusion tubes incorporated in the TAL PALINDROME or MAHURKAR MAXID made available by Covidien. Another suitable catheter tube is disclosed in commonly assigned U.S. patent application Ser. No. 11/528,913, filed Sep. 25, 2006, or commonly assigned U.S. Patent Publication No. 2005/0267400 to Haarala filed Feb. 11, 2005, the entire contents of each application being incorporated herein by reference. Catheter 200 is a hemodialysis catheter having dual lumens. First and second stylet members 104, 106 are received within individual lumens 202 of catheter 200 and advanced within the lumens 202 until stylet hub 102 contacts the proximal or trailing end 204 of the catheter 200. Thereafter, first and second segment members 112, 112b of stylet hub 102 are advanced within the lumens 202 of the catheter. During insertion, locking detents 114 frictionally engage the internal surfaces defining each lumen 202 of catheter 200. In one embodiment, catheter 200 may include an internal shelf 206 within each lumen 202. Locking shelf(s) 206 may cooperatively engage locking detents 114 of catheter connector end 112 to enhance the attachment of catheter 200 to stylet hub 102. Other locking arrangements are also envisioned. In the assembled condition, first and second stylet members 104, 106 extend beyond the distal end of catheter 200.

The use of stylet instrument 100 will now be discussed in terms of a reverse tunneling procedure in connection with hemodialysis treatment. The preferred application will be discussed in terms of deploying a catheter 200 through the right jugular vein for positioning of within the right atrium. As appreciated, the catheter may be implanted in the right atrium via the left jugular vein, the right atrium through the right subclavian vein, the right atrium through the left subclavian vein, or implanted in the femoral vein of the subject.

Referring now to FIGS. 5 and 5A, the internal jugular vein is located and punctured with an introducer needle and a guidewire may be inserted into the vessel using known techniques. The needle is removed and the opening 300 from the skin to the vessel is enlarged adjacent to and along the pathway of the guidewire into the vessel so that a catheter may be inserted into the vessel. A dilator may be positioned over the guidewire and advanced to dilate the vein 502. The dilator is then removed.

Stylet instrument 100, in the assembled condition with catheter 200, is advanced along the guide wire to be passed through the opening 300, and advanced through the jugular vein and the superior vena cava to thereby position the leading end 208 of the catheter 200 within the right atrium 506. The guide wire is then removed from the catheter 200 and the stylet instrument 100, leaving the leading end 208 of catheter 200 in position accessing the right atrium 506.

Figure 6:
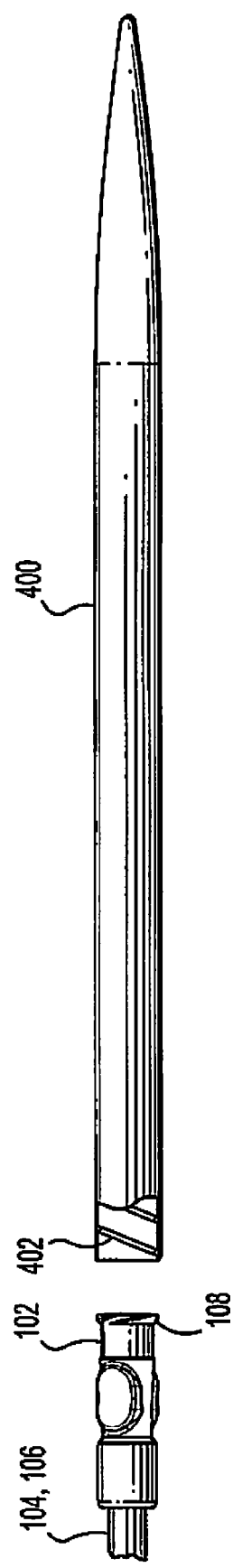
FIG. 6 is a side plan view of a tunneling instrument and the hub illustrating mating connection of the two components.

The positioning of catheter 200 may be confirmed with an x-ray if desired. The trailing end 204 of catheter 200 may extend from the venotomy site 300, as shown in FIG. 5. The clinician may make an exit opening 308 spaced apart from entry opening 300. In one approach, as depicted in FIG. 6, a trocar or tunneler 400 having a locking mechanism 402 at its proximal end may be connected to stylet hub 102 of stylet instrument 100. The locking mechanism of the tunneler 400 may be internal thread 402 which cooperates with the thread of luer connector 108 of stylet hub 102 to connect the tunneler 400 with insertion stylet 100. Other locking mechanisms are envisioned including bayonet couplings, snap fits or the like. Tunneler 400 is then introduced within the venotomy site 300 and advanced toward the exit opening 308 correspondingly pulling the assembled stylet instrument 100 with catheter 200 through the subcutaneous tunnel. In this particular procedure, catheter 200 is devoid of a catheter housing and/or extension tubes. Trocar or tunneler 400 is exposed from exit opening 308 to expose the stylet hub 102 and the trailing end 204 of catheter tube 200. Tunneler 400 is released from stylet instrument 100. At this juncture in the reverse tunneling procedure, insertion stylet 100 is removed from catheter 200. A multiple tube connection source of fluid either irrigation fluid or a source of vacuum may be connected to the catheter hub to perform flushing or aspiration functions within the lumens of the catheter tube. Once the desired functions are completed, proximal end or trailing end 204 of catheter 200 is then connected to a multiple tube connection assembly, or a catheter hub, which is coupled to a hemodialysis machine to perform the hemodialysis procedure.

Figure 5C:
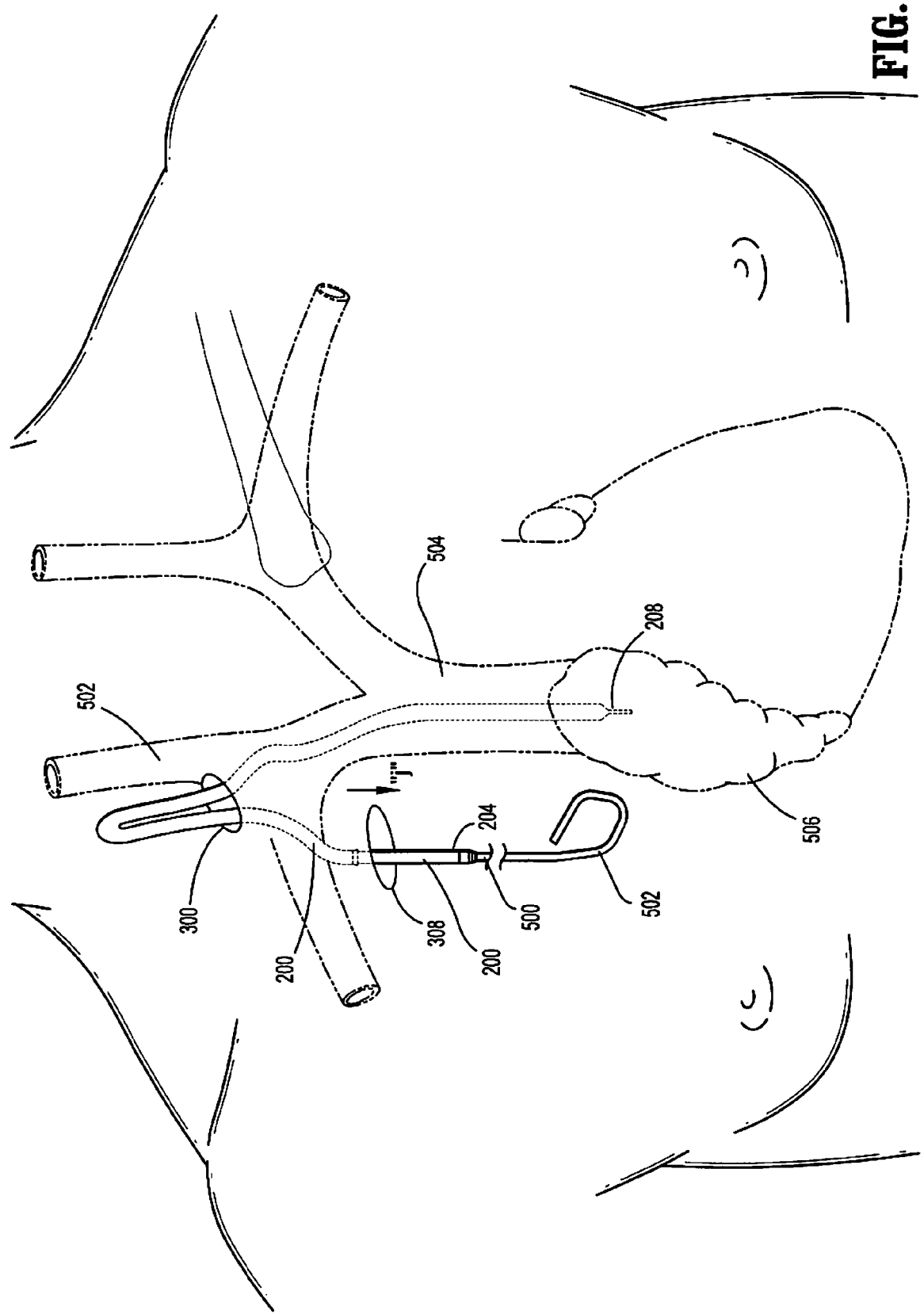

With reference to FIGS. 5B and 5C, in another tunneling procedure, the clinician places the leading end 208 of the catheter 200 within the right atrium following the procedure described above. The subcutaneous tunnel, however, is created by advancing a trocar 500 from exit opening 308 toward the venotomy site or opening 300. Trocar 500 includes handle 502 on its proximal end and, e.g., a female threaded coupling at its distal end similar in arrangements to internal thread 402 of tunneler 400 discussed hereinabove. Trocar or tunneler 500 may includes tapered removable cover 504 enclosing the internal thread. To make the subcutaneous tunnel, the clinician grabs trocar 500 by handle 502, introduces the trocar 500 through exit opening 308 and moves the trocar 500 toward venotomy site or opening 300 until the distal end and cover 504 exits the subject's body through initial venotomy site or opening 300. Thereafter, the clinician removes cover 504 and connects the distal end of the trocar to the stylet hub 102 of the insertion stylet 100 through, e.g., threaded engagement discussed hereinabove. Since the insertion stylet 100 is already coupled to the catheter 200, the connection of the stylet hub 102 to the trocar 500 effectively interconnects the catheter 200 to the trocar 500. Once the catheter 200 is properly secured to the trocar 500, the clinician moves the trocar 500 from the initial opening 300 to the exit opening 308 until the trailing end 204 of the catheter 200 is exposed. The clinician may then release the trocar 500 from the insertion stylet 100. Subsequently, the clinician fluidly connects the proximal end 204 of catheter 200 to a hemodialysis machine to perform the hemodialysis procedure. To establish fluid communication between the hemodialysis machine and the proximal end 204 of catheter 200, the clinician may couple a catheter hub to the proximal end 204 of catheter 200 and then connect the catheter hub to the hemodialysis machine. Alternatively, the clinician may fluidly link the catheter 200 to the hemodialysis machine by employing any suitable fluid communication apparatus such as a multiple tube connection assembly.

Figure 7:
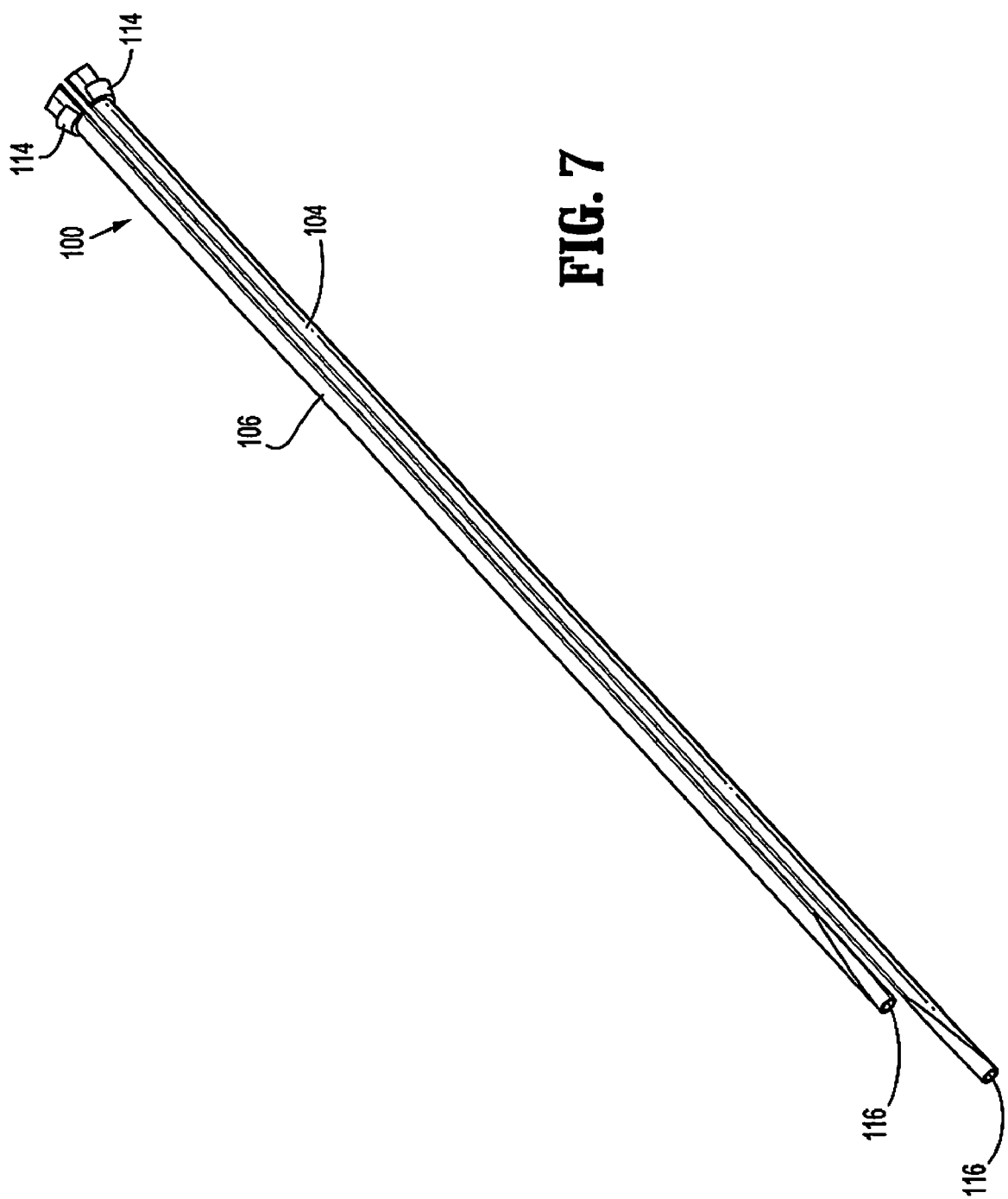
FIG. 7 is a perspective view of an insertion stylet in accordance with an alternate embodiment of the present disclosure.

In an alternate embodiment, first and second stylet members 104, 106 are not connected to a stylet hub, as shown in FIG. 7. Rather, first and second stylet members 104, 106 are individually inserted into a respective lumen 202 of catheter 200. Each of the first and second stylet members 104, 106 incorporates a locking detent 114 positioned at a proximal end thereof. Locking detents 114 are configured to engage the internal surfaces defining lumens 202 of catheter 200, thereby establishing a frictional secured relation between catheter 200 and each of the first and second stylet members 104, 106. First and second stylet members alternatively may include any other suitable device, component, or feature for facilitating connection to catheter 200. Moreover, first and second stylet members 104, 106 may be coupled to each other to provide additional stability. In operation, a clinician may selectively insert first and second stylet members 104, 106 into respective lumens 202 of catheter. During insertion, locking detents 114 frictionally engage the internal surface of catheter 200 and secure first and second insertion stylet 104, 106 to catheter 200.

Figure 8:
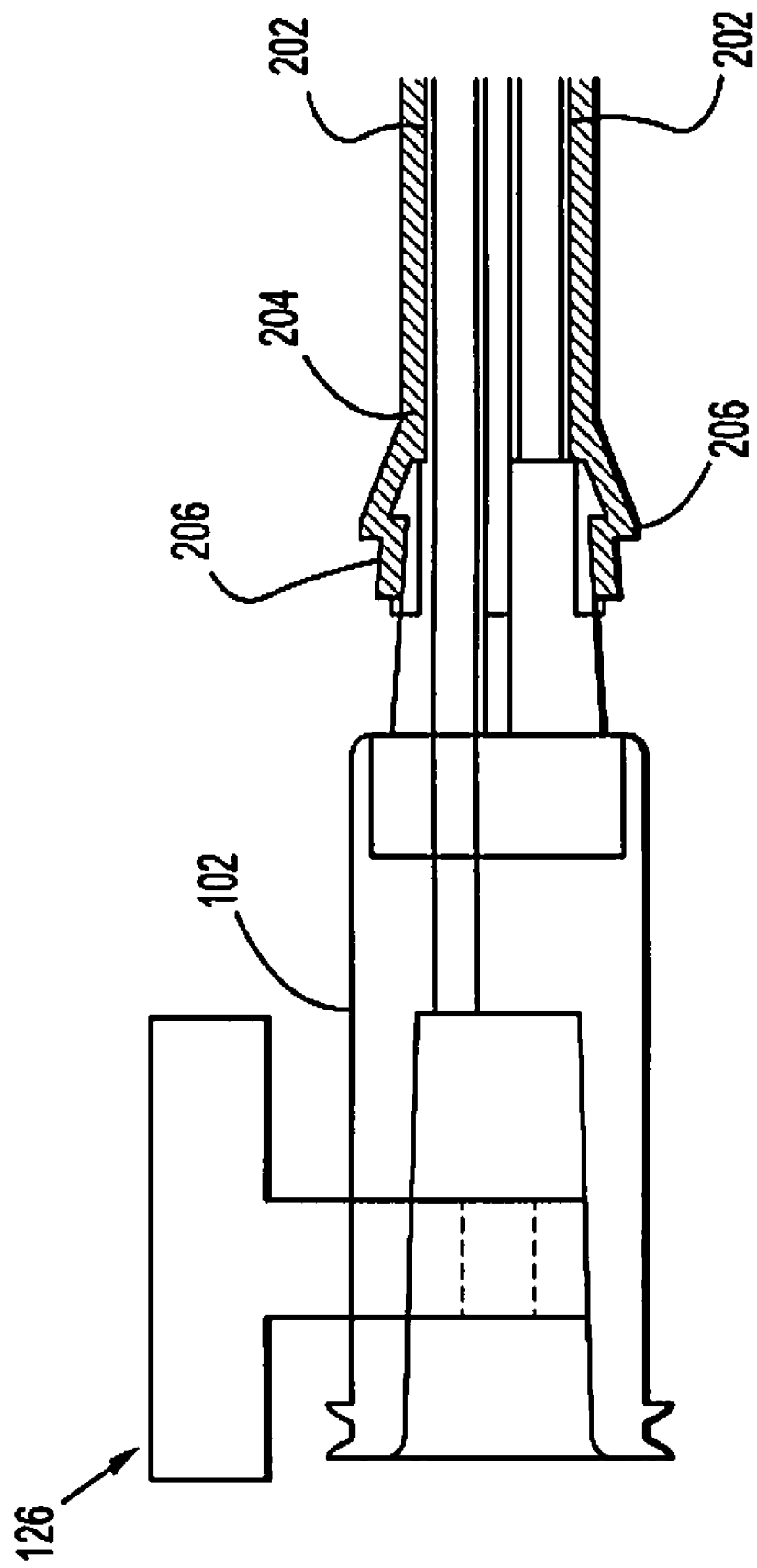
FIG. 8 is a cross-sectional view of an insertion stylet in accordance with an alternate embodiment incorporating a hub with a valve.

FIG. 8 illustrates a further embodiment of the presently disclosed insertion stylet 100. In this embodiment, stylet hub 102 incorporates an internal valve 126 for controlling fluid flow therethrough. Alternatively, stylet hub 102 may be externally connected to a valve. Valve 126 may be placed in first and second positions. In the first position, valve 126 allows fluid flow through the stylet hub 102. Conversely, in the second position, valve 126 precludes fluids from traveling through the stylet hub 102. When placed in the second position, valve 126 prevents fluids leakage and air entry.

As a further embodiment, first and second stylet members 104, 106 may be correspondingly dimensioned such that when positioned within the lumens 202 of the catheter 200, the first and second stylet members 104, 106 occlude the catheter 200 so no other additional sealing means are needed.

Figure 9:
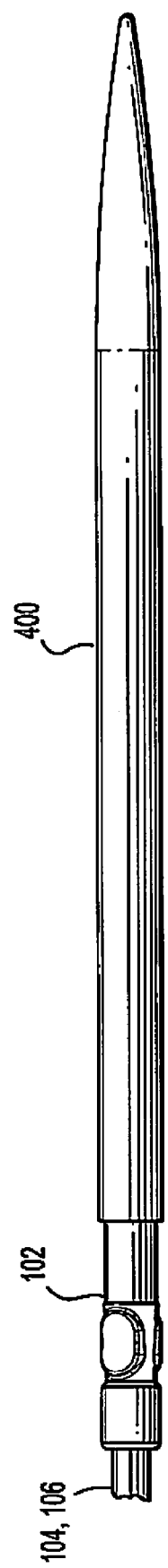
FIG. 9 is a side plan view of a tunneling instrument integrally formed with the insertion stylet.

In another embodiment, insertion stylet 100 has a tunneler 400 integrally formed therewith, as depicted in FIG. 9. The tunneler 400 may be molded to stylet hub 102.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A stylet instrument for facilitating the insertion of a catheter tube through a subcutaneous tunnel, the stylet instrument comprising:

a stylet hub having a first end portion adapted for releasable connection to an external device and a second end portion adapted for releasable connection to a catheter tube, the second end portion comprising a catheter connector adapted to engage the catheter tube, the catheter connector including a first segment and a second segment dimensioned for reception within respective lumens of the catheter tube and at least one locking detent configured to releasably engage an internal surface of the catheter tube, and the stylet hub defining an internal chamber;

first and second stylet members secured to and extending from the stylet hub such that the stylet members can be inserted into the catheter tube while connected to the stylet hub, each of the first and second stylet members being longer than the stylet hub and dimensioned for reception within corresponding lumens of the catheter tube and to extend from a proximal end of the catheter tube to a position adjacent a distal end of the catheter tube, the first stylet member defining a first lumen extending along at least a portion of a first length thereof and the second stylet member defining a second lumen extending along at least a portion of a second length thereof.

2. The stylet instrument according to claim 1, wherein the first end portion of the hub is adapted for connection to a fluid source.

3. The stylet instrument according to claim 2, wherein the first end portion of the hub includes a luer connector and is in fluid communication with the internal chamber.

4. The stylet instrument according to claim 1, wherein the first end portion of the hub is adapted for connection to a trocar.

5. The insertion stylet according to claim 1, wherein the first end portion of the hub includes an external thread adapted to engage a corresponding thread of the external device.

6. The stylet instrument according to claim 1, wherein the first stylet member has a first length and the second stylet has a second length, the first length being greater than the second length.

7. The stylet instrument according to claim 6, wherein the first stylet member includes a lateral opening on an outer wall, the lateral opening being in fluid communication with the lumen of the first stylet member.

8. The stylet instrument according to claim 7, wherein the lateral opening is positioned proximally with respect to the distal opening of the first stylet member.

9. The stylet instrument according to claim 1, wherein each of the first and second stylet members has inlet and outlet ends, and wherein at least one of the first and second stylet members includes a chamfered surface adjacent the corresponding outlet end.

10. The insertion stylet according to claim 1, further including a trocar integrally formed with the hub.

11. The insertion stylet according to claim 1, wherein the hub includes a valve for controlling fluid flow therethrough.

12. The stylet instrument according to claim 1, wherein the first and second stylet members extend beyond a distal end of the catheter tube.

13. A stylet instrument for facilitating the insertion of a catheter tube through a subcutaneous tunnel, the stylet instrument comprising:
a stylet hub having a first end portion adapted for releasable connection to an external device and a second end portion adapted for releasable connection to a catheter tube, the second end portion comprising a catheter connector adapted to engage the catheter tube, the catheter connector including a first segment and a second segment dimensioned for reception within respective lumens of the catheter tube, wherein at least one of the first and second segments of the catheter connector has a tapered configuration for facilitating insertion into the lumens of the catheter tube, and the stylet hub defining an internal chamber;
first and second stylet members secured to and extending from the stylet hub such that the stylet members can be inserted into the catheter tube while connected to the stylet hub, each of the first and second stylet members being longer than the stylet hub and dimensioned for reception within corresponding lumens of the catheter tube and to extend from a proximal end of the catheter tube to a position adjacent a distal end of the catheter tube, the first stylet member defining a first lumen extending along at least a portion of a first length thereof and the second stylet member defining a second lumen extending along at least a portion of a second length thereof.

14. A stylet instrument comprising:
a stylet hub having a first end portion and a second end portion, the first end portion including an integrally formed luer connector configured for releasable securement with an external device, and the second end portion including an integrally formed catheter connector configured for releasable securement with a catheter tube, the catheter connector including at least one locking decent configured to releasably engage an internal surface of the catheter tube; and
first and second stylet members operably connected to, and extending from, the stylet hub, the first and second stylet members being longer than the stylet hub and dimensioned for reception within the catheter tube and to extend from a proximal end of the catheter tube to a position adjacent a distal end of the catheter tube such that the stylet members can be inserted into the catheter tube while connected to the stylet hub.

15. The stylet instrument according to claim 14, wherein the luer connector includes a thread adapted to engage a corresponding thread of the external device.

16. The stylet instrument according to claim 14, wherein the catheter connector includes a first segment and a second segment dimensioned for reception within respective lumens of the catheter tube.

17. The stylet instrument according to claim 14, wherein the first and second stylet members are integral with the stylet hub.

18. The stylet instrument according to claim 14, wherein the first and second stylet members extend beyond a distal end of the catheter tube.

19. A stylet instrument comprising:
a stylet hub having a first end portion and a second end portion, the first end portion including an integrally formed luer connector configured for releasable securement with an external device, and the second end portion including an integrally formed catheter connector configured for releasable securement with a catheter tube, the catheter connector including a first segment and a second segment dimensioned for reception within respective lumen of the catheter tube, wherein at least one of the first and second segments of the catheter connector has a tapered configuration for facilitating insertion into the lumens of the catheter tube; and
first and second stylet members operably connected to, and extending from, the stylet hub, the first and second stylet members being longer than the stylet hub and dimensioned for reception within the catheter tube and to extend from a proximal end of the catheter tube to a position adjacent a distal end of the catheter tube such that the stylet members can be inserted into the catheter tube while connected to the stylet hub.

* * * * *